US00PP17078P2

(12) United States Plant Patent
Lemon

(10) Patent No.: US PP17,078 P2
(45) Date of Patent: Sep. 5, 2006

(54) ***GERANIUM* PLANT NAMED 'CANDY ROSE SPLASH'**

(50) Latin Name: *Pelargonium ×hortorum*
Varietal Denomination: Candy Rose Splash

(75) Inventor: David G. Lemon, Lompoc, CA (US)

(73) Assignee: Oglevee, Ltd,, Connellsville, PA (US)

( * ) Notice: Subject to any disclaimer, the term of this patent is extended or adjusted under 35 U.S.C. 154(b) by 0 days.

(21) Appl. No.: 11/177,050

(22) Filed: Jul. 8, 2005

(51) Int. Cl.
*A01H 5/00* (2006.01)

(52) U.S. Cl. ..... Plt./329

(58) Field of Classification Search ..... Plt./329, Plt./328

See application file for complete search history.

*Primary Examiner*—Kent Bell
(74) *Attorney, Agent, or Firm*—The Webb Law Firm

(57) ABSTRACT

'Candy Rose Splash' is a new variety of *geranium* having dark leaves, vigorous growth, and brightly colored pink flowers.

1 Drawing Sheet

Botanical classification: *Pelargonium×hortorum.*
Varietal denomination: 'Candy Rose Splash'.

BACKGROUND OF THE INVENTION

The present invention comprises a new and distinct cultivar of *Pelargonium×hortorum* known by the varietal name 'Candy Rose Splash'. The new variety was discovered in Lompoc, Calif. The new variety is a result of cross breeding Seedling #2501, known as Rose/Eye, (female parent) (unpatented) and 'Valentine' (male parent) (U.S. Plant Pat. No. 10,587). The purpose of the breeding program was to introduce a high quality dark-leaved zonal *geranium*. The new variety exhibits similar flower color to both parents. The new variety also exhibits a similar dark leaf color to the female parent and has more vigor than the female parent. Also, 'Candy Rose Splash' has a darker leaf color than the male parent. 'Candy Rose Splash' has a similar flower color and leaf color to 'Eclipse Rose Splash', but exhibits more vigor with a better outdoor performance. The new variety was first asexually reproduced by cuttings in Connellsville, Pa. The new variety has been trial and field tested and has been found to retain its distinctive characteristics and remain true to type through successive propagations.

The new variety was grown in a glass greenhouse in a 4" pot in Connellsville, Pa. using full light, 16° C. night temperature and 20° C. day temperature and grown in a soilless media with constant fertilizer at 200 ppm nitrogen and potassium. The new variety exhibits developed roots at 17 days at an average temperature of 23° C. and has a response time of six to seven weeks from a rooted cutting to flowering in a 10 cm. container.

DESCRIPTION OF THE DRAWING

The accompanying photographic drawing illustrates the new variety, with the color being as nearly true as is possible with color illustrations of this type.

DESCRIPTION OF THE PLANT

Figure 1:
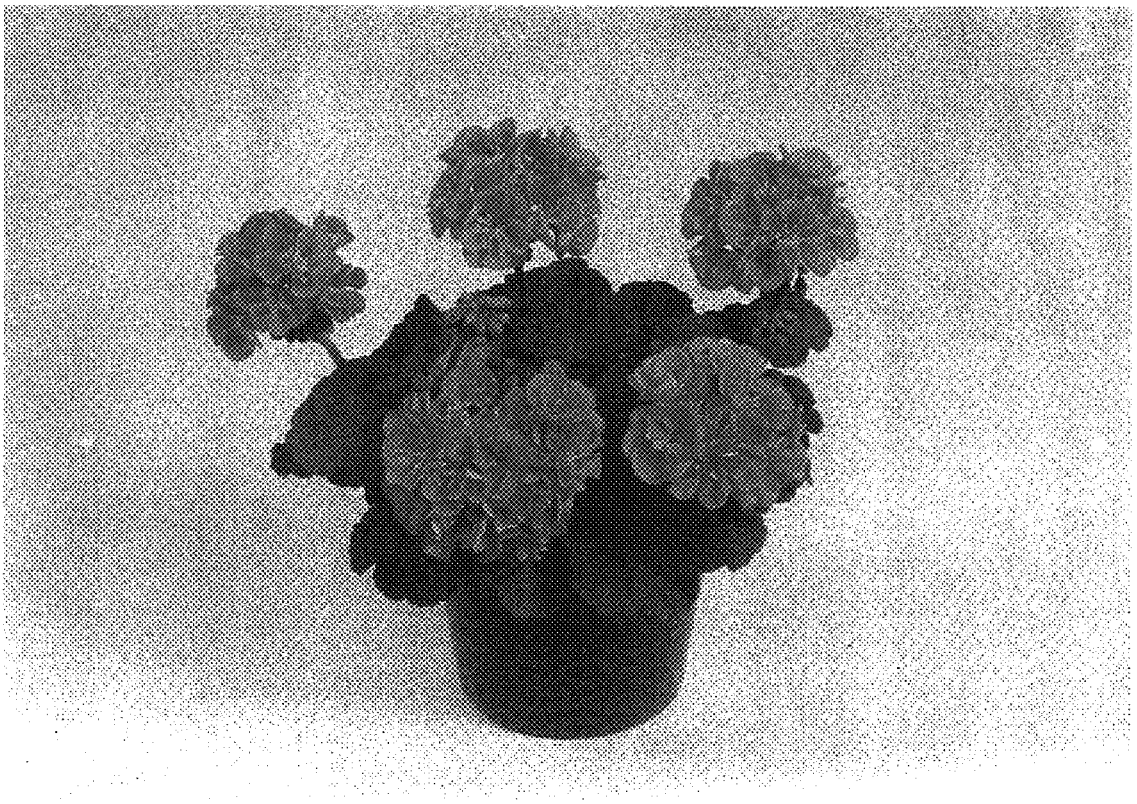

The following detailed description sets forth the characteristics of the new cultivar. The data which defines these characteristics were collected by asexual reproductions carried out in Connellsville, Pa. The color readings were taken indoors under 200–220 foot candles of cool white fluorescent light. The new variety was eight weeks from a rooted cutting when described. Color references are primarily to the 1966 R.H.S. Colour Chart of The Royal Horticultural Society of London.

PLANT

Market class: Zonal.
Time to initiate roots: About 3 days at about 23° C.
Time to develop roots: About 17 days at about 23° C.
Time to produce a finished flowering plant from a rooted cutting: About 6–7 weeks in a 10 cm. container.
Rooting habit: Good, normal.
Form: Round-mounded.
Height from media surface to top of foliage: 13.5–15.5 cm.
Height from media surface to top of flowers: 30.5–32.0 cm.
Plant diameter: 24.0–26.0 cm.
Strength (need for artificial support): No artificial support is needed.
Branching habit: Free branching.
Stem:
- *Main stem length.*—12.5–15.5 cm.
- *Diameter.*—0.8–0.9 cm.
- *Color.*—Yellow-Green Group 144A.
- *Texture.*—Leathery texture.
- *Pubescence.*—Present.
- *Internode length.*—2.2–3.2 cm.

Lateral branches:
- *Length.*—Primary: 3.5–9.0 cm. Secondary: Plant is too young to measure.
- *Diameter.*—Primary: 0.7–0.85 cm. Secondary: Plant is too young to measure.
- *Internode length.*—1.8–2.8 cm.
- *Texture.*—Leathery.
- *Pubescence.*—Present.
- *Color.*—Yellow-Green Group 144A.

Foliage:
- *Arrangement.*—Alternate.
- *Stipules.*—Size: 0.9 cm. high by 0.7 cm. wide. Color: Yellow-Green Group 144A.
- *Zone.*—None present.
- *Size of leaf.*—Length: 5.0–6.4 cm. Width: 5.6–7.3 cm.
- *Shape of leaf (generally).*—Reniform with a stalked base.

*Shape of apex.*—Rounded in accordance with reniform leaf shape.
*Shape of base.*—Cordate.
*Texture.*—Velvety.
*Aspect.*—Leaves have a very slight slope increasing from point of connection toward the margin.
*Margin type.*—Crenate.
*Pubescence.*—Upper surface: Moderate. Lower surface: Moderate.
*Color.*—Young leaves: Upper surface: Green Group 137A. Lower surface: Green Group 137C. Mature leaves: Upper surface: Green Group 137A. Lower surface: Green Group 137C.
*Petiole.*—Length: 4.1–7.1 cm. Diameter: 0.2–0.25 mm. Color: Green Group 137C.
*Veins.*—Venation type: Palmate. Color: Upper surface: Green Group 137C. Lower surface: Yellow-Green Group 144A.

INFLORESCENCE

Bud:
*Stage of development when bud characteristics determined.*—Bud shows color at side but sepals are not parting at the tips.
*Shape of cluster.*—Elliptical.
*Diameter of cluster.*—2.4–3.4 cm.
*Number of buds per cluster.*—11–16.
*Shape of individual bud.*—Ellipse.
*Length of individual bud.*—0.9–1.0 cm.
*Width of individual bud.*—0.6–0.7 cm.
Natural flowering season: Year round horticultural greenhouse crop.
Blooming habit: Continuous, free-flowering.
Umbel diameter: 9.9–11.1 cm.
Umbel depth: 7.8–9.2 cm.
Borne: Umbel, flowers on pedicel, pedicel on peduncle.
Inflorescence position: Above foliage.
Number of inflorescences per lateral branch: 1–3.
Lastingness of an individual flower: 10–14 days.
Florets:
*Form.*—Flat and slightly cupped. As the flowers mature, the florets gradually become more open/flat.
*Number per umbel.*—13–26.
*Diameter.*—4.2–5.0 cm.
*Depth.*—1.5–2.2 cm.
Petals:
*Color.*—The top two petals of the floret have a darker eye and deeper colors than the bottom petals. Upper surface: The top two or three petals are Red-Purple Group 68A on the outer margin moving towards the center. There is a Red-Purple Group 57A eye in the bottom half of the petal. Red-Purple Group 64B colored venation is present throughout the petal, darkest in the bottom ⅓. After the eye the color immediately changes to White Group 155D. The bottom petals are Red-Purple Group 68A with Red-Purple Group 67A speckling. There is a smaller but pronounced Red-Purple Group 57A eye in the bottom petals as well. After the eye the color changes to a Red-Purple Group 73C and slowly changes to White Group 155D. The venation present is Red-Purple Group 64B. Lower surface: The lower surface of the upper petals is Red-Purple Group 73C with heavy speckling of Red-Purple Group 67B. Red-Purple Group 64B colored venation is present. The connection point is White Group 155D. The margin of the bottom petals is Red-Purple Group 68A and slowly fades to Red-Purple Group 73D at the center of the petal. The venation is Red-Purple Group 66B. The point of connection is White Group 155D.
*Shape.*—Inverted teardrop.
*Length.*—2.1–2.8 cm.
*Width.*—1.4–2.1 cm.
*Apex shape.*—Smooth and rounded.
*Base shape.*—Tapered to a point.
*Margin.*—Entire; smooth.
*Number per floret.*—7–9.
*Texture.*—Smooth.
*Tonality from a distance.*—Neon pink flowers with a cherry red eye atop of mounding dark green foliage.
Petaloids:
*Quantity.*—0–1 per floret.
*Shape.*—Splits in a two-pronged unit or are tubular.
*Color* (*upper and lower surface*).—Upper surface is Red-Purple Group 73A and fades to White Group 155D near the point of connection. Lower surface is Red-Purple Group 73C and fades to White Group 155D near the point of connection.
*Length.*—0.9–1.6 cm.
*Width.*—0.1–0.9 cm.
Pedicel:
*Length.*—2.3–3.1 cm.
*Diameter.*—0.15–0.20 cm.
*Color.*—Greyed-Purple Group 185A where the pedicel connects to the floret and fades to Yellow-Green Group 144A as the pedicel approaches the point where it connects to the peduncle.
Peduncle:
*Length.*—14.9–15.9 cm.
*Diameter.*—0.25–0.4 cm.
*Texture.*—A slightly rough leather texture with a moderate amount of pubescence.
*Color.*—Yellow-Green Group 144A with varying Greyed-Purple 185A coloration.
Sepal:
*Number.*—5–6.
*Pubescence.*—Moderate.
*Shape.*—Lanceolate.
*Width.*—0.19–0.4 cm.
*Length.*—0.9–1.0 cm.
Fragrance: No unusual fragrance.
Disease resistance: None observed.
Temperature tolerance: None observed.
Drought tolerance: None observed.

REPRODUCTIVE ORGANS

Stamens:
*Number* (*per flower*).—7–9.
*Filament.*—Length: 0.6–0.9 cm. Color: White Group 155D with the tip being Red-Purple Group 66A.
*Anthers.*—Shape: Oval-like with a slight curve. Length: 0.15–0.2 cm. Color: Grey-Purple Group 183B.
*Pollen.*—Color: Greyed-Orange Group 169A. Amount (generally): Plentiful.
Pistils:
*Number.*—1.
*Length.*—0.8 cm.
*Style.*—Length: 0.3 cm. Color: Red-Purple Group 61A.
*Stigma.*—Shape: Style splits and radiates into 5 parts. Color: Red-Purple Group 61A. Size: 0.1 cm. high.
*Ovaries.*—Completeness: Superior. Pubescence: Present. Length: 0.4 cm. Width: 0.17–0.2 cm. Color: Green Group 137.

I claim:

1. A new and distinct variety of *geranium* plant named 'Candy Rose Splash' as described and illustrated.

* * * * *